United States Patent [19] [11] Patent Number: 5,002,560
Machold et al. [45] Date of Patent: Mar. 26, 1991

[54] EXPANDABLE CAGE CATHETER WITH A ROTATABLE GUIDE

[75] Inventors: Timothy R. Machold, Moss Beach; Michi E. Garrison, Santa Cruz, both of Calif.

[73] Assignee: Advanced Cardiovascular Systems, Inc., Santa Clara, Calif.

[21] Appl. No.: 404,818

[22] Filed: Sep. 8, 1989

[51] Int. Cl.⁵ .............................................. A61M 29/00
[52] U.S. Cl. ..................................... 606/198; 604/95; 604/104
[58] Field of Search ............... 606/159, 191, 192, 194, 606/198, 200; 604/95, 96, 104–109, 164, 170; 600/18

[56] References Cited

U.S. PATENT DOCUMENTS

| | | | |
|---|---|---|---|
| 3,996,938 | 12/1976 | Clark, III | 606/198 |
| 4,572,186 | 2/1986 | Gould et al. | 604/105 |
| 4,577,631 | 3/1986 | Kreamer | 606/198 |
| 4,582,181 | 4/1986 | Samson | 604/95 |
| 4,585,000 | 4/1986 | Hershenson | 604/108 |
| 4,650,466 | 3/1987 | Luther | 606/198 |
| 4,723,549 | 2/1988 | Whaley et al. | 606/194 |
| 4,771,778 | 9/1988 | Mar | 606/192 |
| 4,793,350 | 12/1988 | Mar et al. | 606/195 |
| 4,808,163 | 2/1989 | Laub | 604/105 |
| 4,885,003 | 12/1989 | Hillstead | 604/22 |
| 4,921,484 | 5/1990 | Hillstead | 604/104 |

Primary Examiner—John D. Yasko
Assistant Examiner—A. Gutowski
Attorney, Agent, or Firm—Fulwider, Patton, Lee & Utecht

[57] ABSTRACT

A steerable vascular catheter having an expandable cage mounted on the distal end of a tubular member which is radially expanded and contracted by means of a guidewire which is disposed within an inner lumen in the tubular member and secured to the distal end of the expandable cage. A helical coil is disposed about the secured to a distal portion of the guidewire which extends out the distal end of the expandable cage facilitate steering the catheter through the patient's coronary anatomy. The catheter assembly is particularly adapted to hold open a blood vessel after a vascular procedure therein such as an angioplasty.

11 Claims, 2 Drawing Sheets

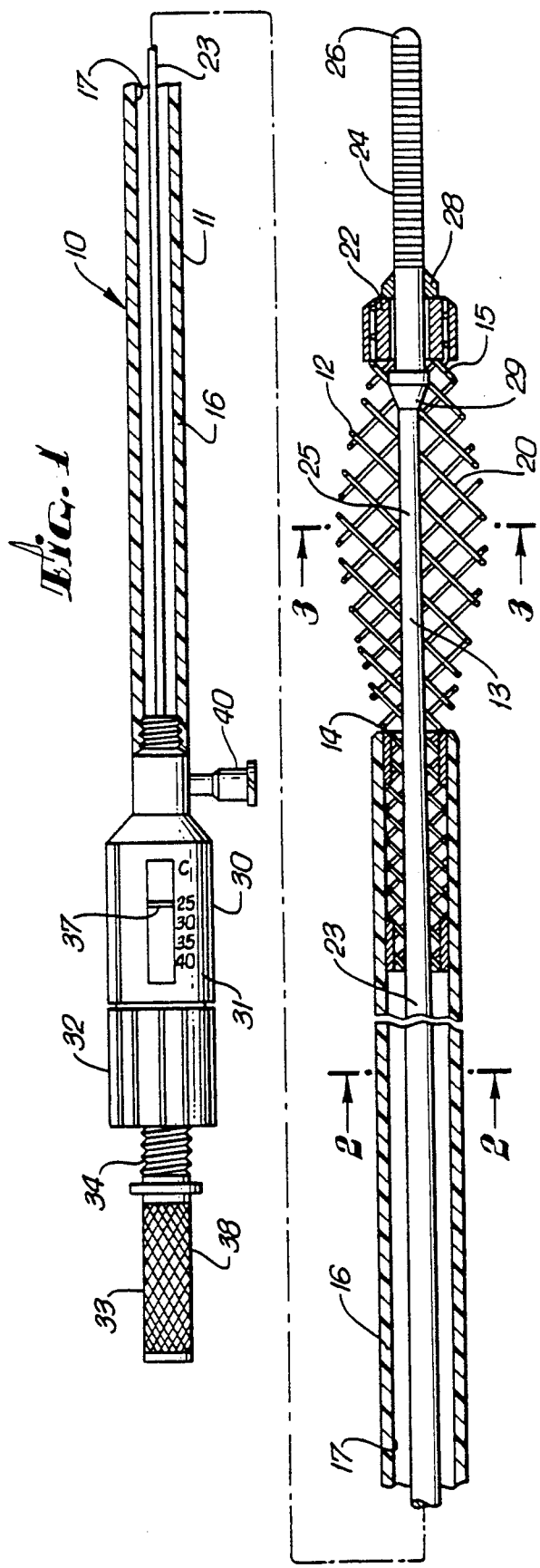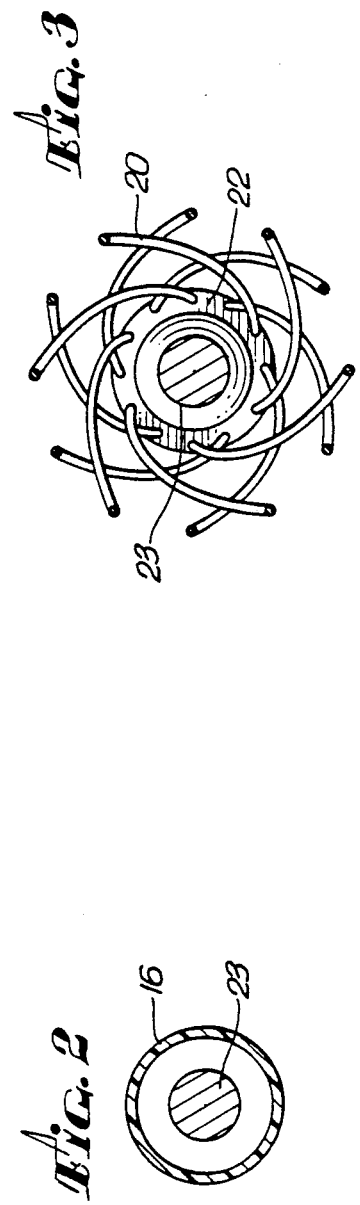

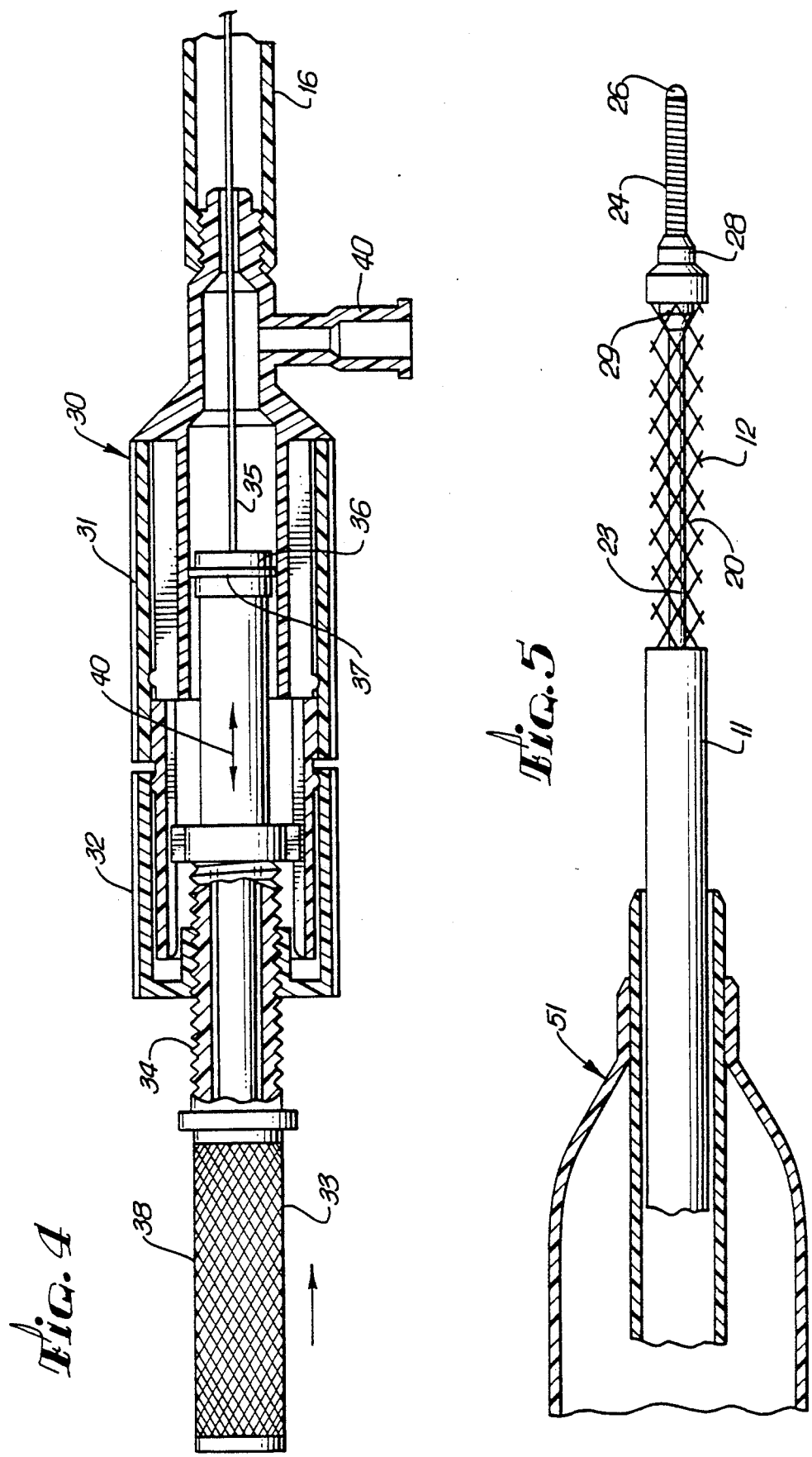

EXPANDABLE CAGE CATHETER WITH A ROTATABLE GUIDE

BACKGROUND OF THE INVENTION

This invention generally relates to vascular catheters suitable for maintaining the patency of a blood vessel after a vascular procedure therein, such as, an angioplasty procedure.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced out of the guiding catheter into the patient's coronary vasculature until the distal end thereof crosses the lesion to be dilated and then the dilatation catheter is advanced over the previously advanced guidewire until the dilatation balloon is properly positioned across the lesion. Once in position across the lesion, the flexible, relatively inelastic balloon is inflated to a predetermined size with radiopaque liquid at relatively high pressures (e.g., greater than about 4 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U.S. Pat. No. 4,323,071 (Simpson-Robert); U.S. Pat. No. 4,332,254 (Lundquist); U.S. Pat. No. 4,439,185 (Lundquist); U.S. Pat. No. 4,168,224 (Enzmann et al.); U.S. Pat. No. 4,516,972 (Samson); U.S. Pat. No. 4,538,622 (Samson et al.); U.S. Pat. No. 4,582,181 (Samson) U.S. Pat. No. 4,597,755 (Samson); U.S. Pat. No. 4,616,652 (Simpson); U.S. Pat. No. 4,748,982 (Horzewski et al.); U.S. Pat. No. 4,771,778 (Mar et al.); U.S. Pat. No. 4,793,350 (Mar et al.), which are hereby incorporated herein in their entirety.

Steerable dilatation catheters with built-in guidewires or guiding elements are being used with greater frequency because the deflated profile of such catheters are generally smaller than conventional dilatation catheters having the same inflated balloon size. Further details of low-profile steerable dilatation catheters may be found in U.S. Pat. No. 4,582,181 (Samson) which is hereby incorporated in its entirety by reference thereto. The lower profile of these catheters allows the catheter to cross tighter lesions and to be advanced much deeper into the patient's coronary anatomy. Moreover, the use of steerable low-profile dilatation catheters having a built-in guidewire or guiding element shortens considerably the time for the angioplasty procedures because there is no need to first advance a guidewire into the patient's coronary anatomy to a desired location therein and then advance a conventional dilatation catheter over the previously inserted guidewire.

Frequently, the stenotic plaque or intima of the blood vessel or both are dissected during angioplasty procedure by the inflation of the balloon, so that upon the deflation of the balloon the dissected lining or flap will collapse, closing off blood flow through the vessel and thereby abruptly stopping or significantly reducing the passage of blood therethrough. In these instances, emergency bypass surgery is usually required to avoid a myocardial infarction distal to the blockage.

A dilatation catheter which also allows for the perfusion of blood distally of the catheter when the balloon is inflated, such as described in U.S. Pat. No. 4,790,315, could be used but such intravascular devices have relatively large profiles which may preclude their advancement through the blockage and thus leave emergency bypass surgery as the only recourse.

Copending application Ser. No. 283,729, filed Dec. 13, 1988, describes an intravascular catheter having an expandable cage on the distal end thereof which is designed to hold a detached lining against an arterial wall for extended periods to facilitate the reattachment thereof. However, this vascular device does not have effective means to guide the device through tortuous coronary anatomy.

What has been needed and heretofore unavailable is a steerable low-profile intravascular device which can be readily advanced through or around a flap which collapses within the bloodstream and which can maintain the patency of the blood vessel by holding the flap against the vessel wall for sufficient time to cause the natural adhesion of the flap to the vessel wall while simultaneously allowing for the perfusion of blood to locations distal to the catheter. The present invention satisfies that need.

SUMMARY OF THE INVENTION

This invention is directed to an improved steerable vascular catheter which has means to maintain the patency of a blood vessel for a long period of time after a vascular procedure and to allow the perfusion of blood through the blood vessel while the blood vessel is held open.

The vascular catheter in accordance with the present invention includes an elongated tubular member having an inner lumen which extends longitudinally over essentially the entire length thereof and which is adapted to receive a guiding member therein. An expandable cage formed by a plurality of spirally arranged strands is secured by the proximal end thereof to the distal end of the tubular member. The distal end of the cage is provided with an opening which allows the guiding member to extend therethrough.

The guiding member extends through the interior of the expandable cage and is connected to the distal end of the expandable cage so that longitudinal movement of the guiding member adjusts the axial spacing between the proximal and distal ends of the expandable cage and thereby changes the radial dimension of the expandable cage. The proximal end of the guiding member is provided with suitable means to longitudinally move the guiding member to effect expansion or contraction of the cage and means to axially rotate the guiding member to steer the catheter through a patient's tortuous vasculature. The means employed to fix the distal end of the expandable cage to the guiding member should allow for the relative axial rotation of the guiding member within the distal end of the expandable cage, so that the catheter can be steered.

The steerable vascular catheter of the invention is easily advanced through a patient's vascular system to a location wherein an occlusion has occurred after a vascular procedure such as angioplasty so that the cage thereof can be expanded within the occlusion to hold the blood vessel open and simultaneously allow blood flow through the cage thereby eliminating or minimizing ischemic conditions distal to the occlusion. Thus, a dissected lining can then be held against the blood vessel wall until it is resecured thereto. These and other advantages of the invention will become more apparent from the following detailed description thereof when taken in conjunction with the accompanying drawings.

BRIEF DESCRIPTION OF THE DRAWINGS

FIG. 1 is an elevational view partially in section of an intravascular catheter assembly embodying features of the invention;

FIG. 2 is a transverse cross-sectional view of the catheter shown in FIG. 1, taken along the lines 2—2;

FIG. 3 is a transverse cross-sectional view of the catheter shown in FIG. 1 taken along the line 3—3;

FIG. 4 is an enlarged view in section of the manipulator on the proximal end of the catheter assembly shown in FIG. 1; and FIG. 5 is a partial elevational view in section of a conventional dilatation catheter with an intravascular catheter assembly as shown in FIG. 1-3 extending through and out of the distal end thereof.

DETAILED DESCRIPTION OF THE INVENTION

FIGS. 1-3 illustrate an intravascular catheter assembly 10 embodying features of the invention which generally includes an elongated catheter body 11, an expandable cage 12 secured to the distal end of the catheter body and a guiding member 13 for steering the catheter through the patient's vascular system and for adjusting the axial distance between the proximal end 14 and distal end 15 of the expandable cage 12 to vary the radial expansion thereof.

The elongated catheter body 11 includes a tubular member 16 with an inner lumen 17 which extends through essentially the entire length of the tubular member and which is adapted to receive guiding member 13.

The expandable cage 12 is formed from a plurality of spirally arranged wires 20, preferably made of stainless steel, or a highly radiopaque material such as platinum-detailed nickel alloy, which have diameters from about 0.001 to about 0.005 inch, preferably about 0.002 to about 0.004 inches. To facilitate fluoroscopic observation of the cage within the patient, radiopaque wires should be at least 0.0025 inch in diameter. The number of wires 20 forming the cage 12 can vary but typically from 4 to about 20 wires are used. The proximal ends of the wires 20 are fixed within the distal end of the catheter body 11 and the distal ends of the wires are bonded together in a suitable manner, such as welding, soldering, or brazing to collar 22 at the distal end 15 of the cage 12 through which the guiding member 13 extends.

The guiding member 13 generally comprises a core member 23, a helical coil 24 or other flexible body disposed about and fixed to the tapered distal portion 25 of the core member 23. A smooth rounded plug 26, preferably formed of radiopaque material, is provided at the distal tip of the coil 24. The construction of the distal portion of the guiding member 13 can be conventional with the core member 23 extending to the plug 26 or the core member can terminate short of the plug and a shaping ribbon (not shown) can extend from the core member 23 to the plug 26 (i.e., a floppy construction). The guide member 13 extends through the inner lumen 17 within the tubular member 16, through the interior of the expandable cage 12 and out the distal end thereof through the passageway in the slidable collar 22 which is sized to allow the core member 23 to rotate therein. Collars 28 and 29 fixed to the core member 23 on both sides of slidable collar 22 prevent relative longitudinal movement therebetween. Collar 28 may be formed by the brazement or weldmemt which bonds the coil 24 to the core member 23. Proximal movement of the guide member 13 will reduce the axial distance between ends 14 and 15 of the cage 12, thereby expanding the cage, and distal movement of the guide member 13 will increase the axial distance between the ends of the cage thereby contracting the cage.

As shown in FIGS. 1 and 4, a manipulator 30 is provided on the proximal end of the catheter body 11 which includes a housing 31, an internally threaded cap 32, and a torquing member 33. An externally threaded element 34 is rotatably mounted about the torquing element 33 with the threads thereof engaging the internal threads of the cap 32. The proximal end 35 of the core member 23 is secured to the distal end 36 of the torquing member. Rotation of the cap 32 causes the longitudinal movement of the externally threaded member 34. The torquing member 33, which freely rotates within the externally threaded member 34, is longitudinally moved, as indicated by arrow 41 shown in FIG. 4, which in turn moves the core member 23, thereby changing the axial spacing between the ends 14 and 15 of the expandable cage 12 and as a result the radial dimension of the cage. An O-ring 37 which is used to seal the distal end 36 may also be used as a marker to indicate the amount of cage expansion, e.g., in millimeters, as shown in FIG. 1 on the exterior of the housing 31. The knob 38 is axially rotated to rotate the core member 23 and the helical coil 24 which is usually shaped to steer the catheter device 10 through a patient's vasculature.

A side arm 40 is provided on the housing 31 to inject heparinized saline solution or other fluids through the inner lumen 17 to keep the lumen free of blood and to prevent the formation of thrombus in the lumen or the expandable cage 12.

Generally, the dimensions of the catheter assembly of the invention are very similar to the dimensions of vascular catheters used in angioplasty procedures. The overall length of the assembly may be about 100 to about 175 cm. The diameter of the tubular member 16 may range from about 0.03 to 0.06 inch. The expandable cage 12 in the unexpanded condition has approximately the same diameter as the tubular member 16 but may be expanded to a maximum diameter of about 1 to about 10 mm. The diameter of the inner lumen 17 will generally be slightly larger than the diameter of the core member 23 which will typically be about 0.06 to about 0.018 inch.

The catheter assembly of the present invention may be formed of conventional materials of construction. For example, the tubular member 16 can be made of suitable plastic material such as polyethylene, polyvinylcholoride, polyesters and the like. The section of the tubular member which remains within the guiding catheter during vascular procedures may be formed of suitable metal, such as stainless steel (i.e., hypotubing). The core wire 23 and the wires 20 forming expandable cage 12 are preferably formed of stainless steel but may be formed of other metals or suitable plastics or composites. The coil 24 may be formed of stainless steel or radiopaque alloys such as platinum-nickel to facilitate fluoroscopic observation.

The steerable catheter assembly 10 of the present invention has been designed to be utilized primarily after a vascular procedure such as angioplasty and the use of the vascular device is similar in many respects to the operation of the steerable dilatation catheters disclosed in U.S. Pat. No. 4,582,181; U.S. Pat. No. 4,793,350; and U.S. Pat. No. 4,771,778 to which reference has previously been made. The catheter assembly 10 is advanced through a guiding catheter previously introduced into the patient's femoral or brachial artery with the distal tip of the guiding catheter in the ostium of a coronary artery. The distal portion of the assembly 10 extending out the distal end of the guiding catheter into the patient's coronary artery is steered through the patient's coronary anatomy to an arterial location where a closure has occurred. The cap 32 is rotated to expand the cage 12 to thereby hold the flap against the arterial wall. The cage 12 is held in the expanded condition for a sufficient period of time, e.g., 15 minutes to 24 hours, for the flap to become naturally secured to the arterial wall. Longer period of time, e.g., up to 3 days may also be useful in some circumstances. Usually, the cage 12 must be able to withstand an external pressure of about 4 psi without collapse to ensure that it will be able to hold a flap against the arterial wall. During the period of cage expansion, blood flows readily through the open weave structure of the cage to prevent ischemic conditions distal to the obstruction or in a side branch.

After the flap has been adequately secured to the artery wall, the expanded cage 12 can be elongated by turning the cap 32 in a direction opposite to the direction which causes expansion of the cage to elongate the cage and then catheter assembly 10 can be removed from the patient or advanced further into the patient's vascular system if additional procedures are contemplated.

A particularly attractive embodiment of the invention is illustrated in FIG. 5 wherein the catheter assembly 10 of the invention is constructed to have a maximum diameter which is sufficiently small to fit within the inner lumen 50 of a conventional dilatation catheter 51. In this manner, if, after a dilatation with a conventional angioplasty catheter, an occlusion occurs when the balloon is deflated, the guidewire can be quickly removed and the catheter assembly of the invention can be inserted through the inner lumen 50 until the expandable cage 12 is distal of the occlusion. The catheter assembly 10 may then be pulled proximally until the expandable cage is positioned within the occlusion. The cage 12 is then expanded as previously described to hold the portion of the lining which blocks the blood flow against the arterial wall until it is secured thereto. The catheter assembly of the invention itself may be used in place of a guidewire.

While the invention has been described herein in terms of preferred embodiments, it will be appreciated by those skilled in the art that modifications can be made to the present invention without departing from the scope thereof.

What is claimed is:

1. A steerable vascular catheter for repairing a section of an arterial lining damaged by a vascular procedure which results in an occlusion or a partial occlusion of the artery by maintaining the patency of the damaged arterial lining over an extended period while allowing the perfusion of blood therethrough, comprising:
   (a) an elongated catheter body having an inner lumen extending therethrough;
   (b) an expandable cage secured to the distal end of the catheter body which is formed from a plurality of spirally arranged strands and which has sufficient radial strength in the expanded condition to hold open a damaged arterial section;
   (c) a guiding member rotatably disposed within the inner lumen of the elongated catheter body having a distal portion extending through the interior of the expandable cage and out the distal end thereof with a flexible body disposed about the distal portion of the guiding member which extends out of the distal end of the expandable cage;
   (d) means to secure the distal portion of the guiding member to the distal end of the expandable cage so that there can be essentially no relative longitudinal movement therebetween but which allows the guiding member to rotate within the distal end of the expandable cage;
   (e) means on the proximal end of the guiding member to axially rotate the guiding member so as to rotate the distal portion thereof which extends out the distal end of the expandable cage and thereby steer the catheter within the patient's arterial system;
   (f) means to move the guiding member proximally within the inner lumen of the catheter to decrease the axial spacing between the distal and proximal ends of the expandable cage and thereby increase the radial dimensions thereof and thereby hold open a damaged section of arterial lining and to move the guiding member distally within the inner lumen of the catheter body to increase the axial spacing between the distal and proximal ends of the expandable member to reduce the radial dimension thereof sufficiently to remove the expandable cage from the damaged arterial lining.

2. The vascular catheter of claim 1 wherein the catheter body is a tubular member with at least the distal portion formed of plastic.

3. The vascular catheter of claim 1 wherein the expandable cage is formed from about 4 to about 20 strands.

4. The vascular catheter of claim 1 wherein the strands are wires having diameters from about 0.002 to about 0.005 inch.

5. The vascular catheter of claim 4 wherein the wires are formed from materials selected from the group consisting of stainless steel and platinum-nickel alloys.

6. The vascular catheter of claim 1 wherein the flexible body on the distal portion of the guide member is a helical coil of wire.

7. The vascular catheter of claim 1 wherein the means to secure the guiding member to the distal end of the expandable cage includes a collar having a passageway therein through which the distal portion of the guiding member passes.

8. The vascular catheter of claim 7 wherein the passageway is sufficiently large in diameter to allow the axial rotation of the guiding member therein.

9. The vascular catheter of claim 8 wherein a pair of fittings are provided on the guiding member one distally adjacent the collar and one proximally adjacent the collar to fix the position of the guiding member to the distal end of the cage.

10. A method for repairing a section of a patient's artery which has been damaged by a vascular procedure therein which can result in an occluded or partially occluded artery, comprising:
(a) providing a steerable vascular catheter, comprising:
(i) an elongated catheter body having an inner lumen extending therethrough;
(ii) an expandable cage secured to the distal end of the catheter body which is formed from a plurality of spirally arranged strands and which is adapted to be expanded against the damaged section of the arterial lining to maintain the patency thereof;
(iii) a guiding member rotatably disposed within the inner lumen of the elongated catheter body having a distal portion extending through the interior of the expandable cage and out the distal end thereof with a flexible body disposed about the distal portion of the guiding member which extends out of the distal ned of the expandable cage;
(iv) means to secure the distal portion of the guiding member to the distal end of the expandable cage which prevents relative axial movement therebetween but which allows rotational movement therebetween;
(v) means on the proximal end of the guiding member to axially rotate the guiding member within the inner lumen of the catheter body to rotate the distal end which extends out of the expandable cage and thereby steer the catheter within the patient's arterial system; and
(vi) means on the proximal end to move the guiding member proximally within the inner lumen of the catheter body to decrease the axial spacing between the distal and proximal ends of the expandable cage and thereby increase the radial dimensions thereof and to move the guiding member distally within the inner lumen to increase the axial spacing between the distal and proximal ends of the expandable cage and thereby decrease the radial dimensions thereof;
(b) advancing the catheter through the patient's arterial system while operating the means to rotate the guiding member to steer the distal tip of the catheter until the expandable cage is disposed within the site of the damaged section of the arterial lining;
(c) operating the means to move the guiding member proximally within the inner lumen to reduce the axial distance between the ends of the expandable cage and thereby expand the cage to hold open the damaged section of the arterial lining;
(d) holding the expandable cage in the expanded condition within the damaged section of the arterial lining for an extended period;
(e) operating the means to move the guiding member within the inner lumen to increase the axial distance between the ends of the expandable cage and thereby reduce the radial dimension of the expandable cage; and
(f) removing the catheter from the patient.

11. The method of claim 10 wherein the catheter is advanced through at least part of the patient's arterial system through an inner lumen of a dilatation catheter.

* * * * *